(12) United States Patent
Hendriks et al.

(10) Patent No.: US 12,023,152 B2
(45) Date of Patent: Jul. 2, 2024

(54) TUMOR MARGIN ASSESSMENT

(71) Applicant: KONINKLIJKE PHILIPS N.V., Eindhoven (NL)

(72) Inventors: Bernardus Hendrikus Wilhelmus Hendriks, Eindhoven (NL); Gerhardus Wilhelmus Lucassen, Eindhoven (NL); Klaas Cornelis Jan Wijbrans, Rijen (NL); Jarich Willem Spliethoff, Utrecht (NL); Nijs Cornelis Van Der Vaart, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 920 days.

(21) Appl. No.: 17/049,528

(22) PCT Filed: Apr. 22, 2019

(86) PCT No.: PCT/EP2019/060250
§ 371 (c)(1),
(2) Date: Oct. 21, 2020

(87) PCT Pub. No.: WO2019/206838
PCT Pub. Date: Oct. 31, 2019

(65) Prior Publication Data
US 2021/0251535 A1     Aug. 19, 2021

(30) Foreign Application Priority Data

Apr. 24, 2018 (EP) ..................... 18169011

(51) Int. Cl.
*G16H 50/20* (2018.01)
*A61B 5/00* (2006.01)
(Continued)

(52) U.S. Cl.
CPC ........ *A61B 5/14551* (2013.01); *A61B 5/0059* (2013.01); *A61B 5/0075* (2013.01);
(Continued)

(58) Field of Classification Search
CPC ............ A61B 5/14551; A61B 5/14546; A61B 5/4872; A61B 5/4875; A61B 10/02;
(Continued)

(56) References Cited

U.S. PATENT DOCUMENTS 6,859,282 B1 * 2/2005 Weber ..................... G01N 33/12
356/630
2011/0092823 A1    4/2011 Tearney
(Continued)

FOREIGN PATENT DOCUMENTS

JP        200879835 A     4/2008
WO     2012143816 A1    10/2012

OTHER PUBLICATIONS

Guangyao Li, Zhendong Guo, and Sung-Liang Chen, "Miniature all-optical probe for large synthetic aperture photoacoustic-ultrasound imaging," Opt. Express 25, 25023-25035 (2017) (Year: 2017).*

(Continued)

*Primary Examiner* — David J. McCrosky
*Assistant Examiner* — Clarissa Cuevas (57) ABSTRACT

A system SY for determining a tissue type TY of a tissue region TR is provided in which the distal ends $OFDE_{1..n}$ of at least three optical fibers define a plurality of intersecting optical paths $IOP_{1..k}$ within the tissue region TR. A tissue signal $Q_{1..k}$ indicative of a tissue type TY for the respective optical path $IOP_{1..k}$ is generated from said spectral measurement data SMD corresponding to each of the plurality of intersecting optical paths $IOP_{1..k}$. Each tissue signal $Q_{1..k}$ is compared with a reference threshold QRT for the tissue type, (Continued)

and with an average of the tissue signals QMA. At least a portion of the tissue region is identified as the tissue type TY if i) every tissue signal $Q_{1..k}$ in the tissue region TR indicates that its corresponding tissue is not the tissue type TY in the comparison with the reference threshold QRT and ii) at least one of the tissue signals $Q_{1..k}$ in the tissue region TR lies between the average QMA of the tissue signals $Q_{1..k}$ and the reference threshold QRT, and a difference Δ between the at least one tissue signal $Q_{1..k}$ and the average QMA of the tissue signals $Q_{1..k}$ exceeds a predetermined value ΔP.

20 Claims, 4 Drawing Sheets

(51) Int. Cl.
*A61B 5/145* (2006.01)
*A61B 5/1455* (2006.01)
*A61B 10/02* (2006.01)
*A61B 17/32* (2006.01)
*A61B 17/3211* (2006.01)
*A61M 25/00* (2006.01)
*A61M 25/09* (2006.01)

(52) U.S. Cl.
CPC ........ *A61B 5/0091* (2013.01); *A61B 5/14546* (2013.01); *A61B 5/7264* (2013.01); *A61B 10/02* (2013.01); *A61B 17/320068* (2013.01); *A61B 17/3211* (2013.01); *A61M 25/00* (2013.01); *A61M 25/09* (2013.01); *G16H 50/20* (2018.01)

(58) Field of Classification Search
CPC ........ A61B 17/320068; A61B 17/3211; A61B 18/02; A61B 18/042; A61B 18/14; A61B 2018/00577; A61B 2217/005; A61B 2218/007; A61B 5/4312; A61B 5/7264; A61B 5/0075; A61M 25/00; A61M 25/09; G16H 50/20
See application file for complete search history.

(56) References Cited

U.S. PATENT DOCUMENTS

2014/0378797 A1 12/2014 Hendriks
2017/0156797 A1 6/2017 Hendriks

OTHER PUBLICATIONS

De Boer et al: "Using DRS During Breast Conserving Surgery: Identifying Robust Optical Parameters and Influence of Inter-Patient Variation"; Biomedical Optics Express, Dec. 2016, vol. 7, No. 12, 13 Page Article.
De Boer et al.: "Fat/Water Ratios Measured With Diffuese Reflectance Spectroscopy to Detect Breast Tumor Boundaries"; Breast Cancer Res Treat (2015), 152, pp. 509-518.
Engelhardt et al: "Comparing Classification Methods for Diffuse Reflectance Spectra to Improve Tissue Specific Laser Surgery"; BMC Medical Research Methodology, 2014, 14:91, pp. 1-15.
Farrell et al: "a Diffusion Theory Model of Spatially Resolved, Steady-State Diffuse Reflectance for the Noninvasive Determination of Tissue Optical Properties "; Med Phys. 19(4), Jul./Aug. 1992, pp. 879-888.
Muller et al: "Recovering Intrinsic Fluorescence by Monte Carlo Modeling"; J. of Biomedical Optics, 18(2), 25 Page Document.
Nachabe et al: "Estimation of Biological Chromophores Using Diffuse Optical Spectroscopy: Benefit of Exztending the UV-VIS Wavelength Range to Include 1000 to 1600nm"; Optics Express, vol. 18, No. 24, Nov. 2010, pp. 1432-1442.
Nachabe et al: "Effect of Bile Absorption Coefficients on the Estimation of Liver Tissue Optical Properties and Related Implications in Discriminating Healthy and Tumorous Samples"; Biomedical Optics Express, Mar. 2011, vol. 2, No. 2. No. 3, 15 Page Document.
Nachabe et al: "Estimation of Lipid and Water Concentrations in Scattering Media With Diffuse Optical Spectroscopy From 900 to 1600 nm"; Journal of Biomedical Optics 15(3), May 1/Jun. 2010, pp. 1-1-1-10.
PCT/EP2019/060250 ISR & WO, Aug. 12, 2019, 14 Page Document.

\* cited by examiner

TUMOR MARGIN ASSESSMENT

CROSS-REFERENCE TO PRIOR APPLICATIONS

This application is the U.S. National Phase application under 35 U.S.C. § 371 of International Application No. PCT/EP2019/060250, filed on Apr. 22, 2019, which claims the benefit of European Patent Application No. 18169011.6, filed on Apr. 24, 2018. These applications are hereby incorporated by reference herein.

FIELD OF THE INVENTION

The invention relates to an optical-based system and method for determining a tissue type. More specifically, the optical system and method may be used to identify a tissue type such as healthy tissue, benign tissue, malignant or tumor tissue, fat tissue, muscle tissue, collagen tissue, elastin tissue, nerve tissue, liver tissue, colon tissue, lung tissue, or brain tissue. Whilst the invention may be used in determining a tissue type in the medical field in general, the invention finds particular application in the assessment of a tumor margin during cancer surgery, and may exemplarily be used in breast conservation surgery to ensure adequate tissue removal.

BACKGROUND OF THE INVENTION

In many medical fields it is important to be able to distinguish between different tissue types. In oncology, for example, the distinction between for example healthy, malignant and benign tissue is important in determining how much tissue needs to be removed, and in assessing the type of tissue that has already been removed.

In the example of surgical removal of breast tumors, e.g. lumpectomy, during breast conservation surgery the clinical goal is to completely remove the tumorous tissue. Ideally, tumorous tissue is removed together with a surrounding margin of 1-2 mm (i.e. a negative margin). Any tumorous tissue left behind in the patient (i.e. a positive margin) could lead to tumor recurrence and subsequently the need for additional surgery or radiotherapy. Prior to the surgery an excision plan is typically generated from pre-operative images using e.g. mammography, computed tomography, i.e. CT, magnetic resonance imaging, i.e. MRI, or ultrasound. In the case of non-palpable tumors or when patients are treated with neoadjuvant chemotherapy, a marker is placed in the tumor for guidance during surgery. During surgery a blue dye is injected to locate nearby lymph nodes that are inspected for the presence of tumor cells. Post-surgery, the resected tumor undergoes pathological analysis to determine the completeness of tissue removal, and this typically takes two days.

When performing surgical tumor excision the surgeon uses the markers, the blue dye, tactile feedback of the tissue and a mental map to the pre-operative images to guide the excision. Tumor margins can however be poorly defined, and the lack of accurate guidance and real-time feedback on the tissue type leads to significant percentage of positive margins that require additional surgery or radiotherapy at a later stage.

Various optical techniques have been proposed to address this issue, including the use of diffuse reflectance spectroscopy, i.e. DRS.

A document entitled "Fat/water ratios measured with diffuse reflectance spectroscopy, DRS, to detect breast tumor boundaries" by De Boer, L. L. et al.; Breast Cancer Res Treat (2015) 152:509-518; "De Boer 1", relates to tumor margin recognition in breast conservation surgery using diffuse reflectance spectroscopy. Optical parameters for discriminating tumor from benign tissue are reported. The most suitable optical parameters reported relate to the absorption of fat and water. A fat-to-water ratio in the extended near-infrared wavelength region, approximately 1000-1600 nm, provided the best discrimination between benign and tumor sites and gave a sensitivity and specificity of 100%, excluding the border sites between fat and tumor.

Another document relating to the same DRS optical technique, entitled "Using DRS during breast conserving surgery: identifying robust optical parameters and influence of inter-patient variation" by de Boer, L. L.; et al., Vol. 7, No. 12, 1 Dec. 2016, Biomedical Optics Express 5188; "De Boer 2"; addresses inter-patient variation and changes in tissue physiology occurring during the resection that might hamper this light-based technology. The document reports that measurements taken in-vivo were not significantly different from the measurements taken ex-vivo. The document concludes that DRS is a robust technology for the detection of tumor tissue during breast conserving surgery.

Another document that also relates to DRS, WO2012143816, deals with discrimination of malignant tissue from normal and benign tissue in a single patient on the basis of optical spectroscopic measurements. Starting from spectroscopic measurements in normal tissue, reference values are obtained for the normal class. With spectroscopic measurements in other tissues data points can be assigned to new class(es) when the spectral characteristics fall outside a threshold defining the reference class. Thresholds between different classes can also be defined. Finding the transition to malignant tissue is based on comparing the spectroscopic values to the classification threshold discriminating normal and benign versus malignant tissue. Thus, the basis of normal spectroscopic measurements is tuned to the individual patient characteristic. It is reported that discriminating the normal plus benign and malignant from that reference is more efficient compared to the reference of the all-patient database.

However there remains a need to improve tissue classification using optical techniques.

SUMMARY OF THE INVENTION

The present invention seeks to improve tissue classification using optical techniques. A system and a related computer program product are provided. The system and computer program product find application in the medical field, particularly in oncology, and are described in particular in relation to the exemplary field of breast cancer surgery. It is however to be appreciated that the invention finds application in the wider medical field of tissue classification using optical techniques.

Thereto a system for determining a tissue type of a tissue region is provided as defined in claim 1. The system includes an optical probe, a spectral measurement system and a processing unit. The optical probe has a distal end and at least three optical fibers, each optical fiber having a distal end disposed at the distal end of the optical probe and a proximal end that is in optical communication with the spectral measurement system. The spectral measurement system includes at least one optical source and at least one optical detector. Each proximal end of each optical fiber is in optical communication with one of the at least one optical source or one of the at least one optical detector, and each distal end of each optical fiber is arranged at the distal end of the optical probe such that when the tissue region is in contact with the distal end of the optical probe a plurality of intersecting optical paths are defined within the tissue region between the at least one optical source and the at least one optical detector. The processing unit is in communication with the spectral measurement system and is configured to cause the spectral measurement system to generate spectral measurement data corresponding to each of the plurality of intersecting optical paths, and to generate from said spectral measurement data a tissue signal indicative of a tissue type for the respective optical path. The processing unit is further configured to:

compare each tissue signal with a reference threshold for the tissue type; and to compare each tissue signal with an average of the tissue signals; and to identify at least a portion of the tissue region as the tissue type if i) every tissue signal in the tissue region indicates that its corresponding tissue is not the tissue type in the comparison with the reference threshold and ii) at least one of the tissue signals in the tissue region lies between the average of the tissue signals and the reference threshold, and a difference between the at least one tissue signal and the average of the tissue signals exceeds a predetermined value.

The three or more optical fibers in the optical probe provide intersecting optical paths within the tissue region between the at least one optical source and the at least one optical detector. By providing multiple optical paths a larger surface area, and due to the penetration of the optical paths in the tissue, a larger volume, of tissue region is measured, as compared to for example using a single optical path. This advantageously allows for the rapid measurement of large areas or volumes of tissue, which in the exemplary tissue resection procedure may reduce the number of a times a probe must be positioned on the tissue in order to scan an area. The intersecting optical paths provide for the sampling of a common portion of the tissue region and thereby improves the correlation between the spectral measurement data thus obtained. This helps to reduce the intra-patient variability of the measurements. The possibility of missing a tumor due to blind spots in an optical probe that is sparsely populated with optical fibers at its distal end, is also reduced through the use of the intersecting optical paths.

As is described in more detail later herein, the processing unit causes the spectral measurement system to generate the spectral measurement data corresponding to each optical path, and to generate therefrom a tissue signal indicative of a tissue type for each optical path. The tissue type may for example be "tumor tissue".

Such a determination of tissue type, for single, i.e. non-overlapping optical paths, has previously been reported in De Boer 1, De Boer 2 and WO2012143816, to be subject to large inter-patient variation. These citations advocate the use of a personal threshold rather than an inter-patient, i.e. a population-based threshold to discriminate the tissue type from other tissue types.

In the present invention the processing unit compares each measured tissue signal with a reference threshold for the tissue type. The reference threshold may be a population threshold. The processing unit also compares each measured tissue signal with the average of the measured tissue signals. The number of false negative identifications of the tissue type may be reduced by the processing unit identifying at least a portion of the tissue region as the tissue type if i) every tissue signal in the tissue region indicates that its corresponding tissue is not the tissue type in the comparison with the reference threshold and ii) at least one of the tissue signals in the tissue region lies between the average of the tissue signals and the reference threshold, and a difference between the at least one tissue signal and the average of the tissue signals exceeds a predetermined value.

Thus, the present invention provides improved tissue classification.

In accordance with one aspect the processing unit is further configured to store each tissue signal for a tissue region corresponding to a current position of the optical probe on the tissue, and for one or more tissue regions corresponding to one or more earlier positions of the optical probe on the tissue. In this aspect the predetermined value used for the current position of the optical probe is determined based on the tissue signals for the one or more tissue regions corresponding to the one or more earlier positions of the optical probe. By using a more personalized threshold level in the identification a more specific tissue classification is provided. The predetermined value may for example be determined based on the variation of the tissue signals at the one or more tissue regions corresponding to the one or more earlier positions of the optical probe.

In accordance with another aspect a computer program product is provided. The computer program product includes instructions which when executed on a processor of the processing unit of the system according to claim 1, cause the processor to carry out the method steps of:

causing the spectral measurement system to generate spectral measurement data corresponding to each of the plurality of intersecting optical paths, and to generate from said spectral measurement data a tissue signal indicative of a tissue type for the respective optical path; and comparing each tissue signal with a reference threshold for the tissue type; and comparing each tissue signal with an average of the tissue signals; and identifying at least a portion of the tissue region as the tissue type if i) every tissue signal in the tissue region indicates that its corresponding tissue is not the tissue type in the comparison with the reference threshold and ii) at least one of the tissue signals in the tissue region lies between the average of the tissue signals and the reference threshold, and a difference between the at least one tissue signal and the average of the tissue signals exceeds a predetermined value.

Further aspects are described with reference to the appended claims. Further advantages from the described invention will also be apparent to the skilled person.

DETAILED DESCRIPTION OF THE INVENTION

In order to illustrate the principles of the present invention a system and related computer program product are described with particular reference to the exemplary field of breast cancer surgery. It will however be readily apparent that the application field is not limited to this specific example and that the invention finds application in the wider medical field of tissue classification using optical techniques.

Figure 1:
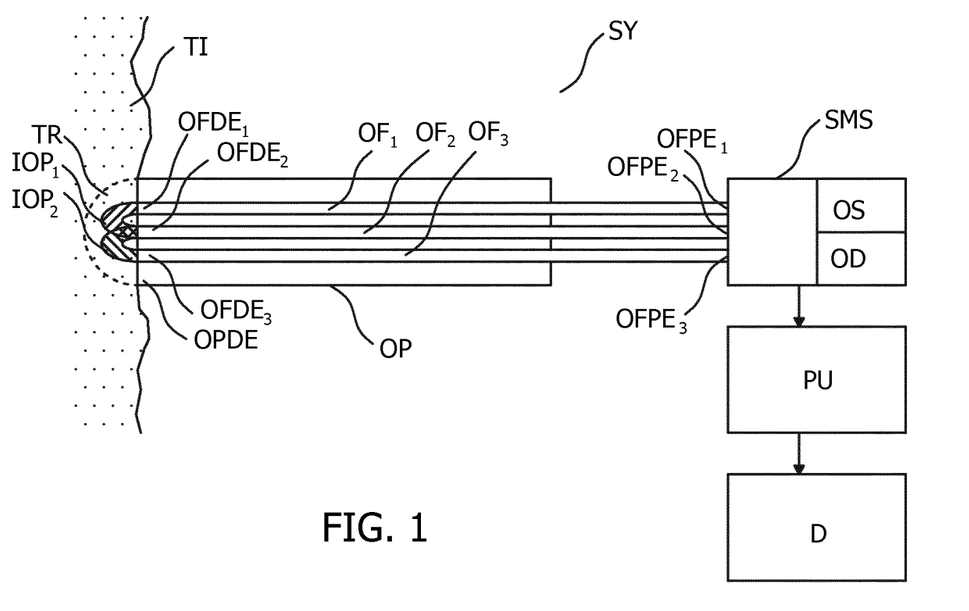
FIG. 1 illustrates a system SY that includes an optical probe OP, a spectral measurement system SMS and a processing unit PU.

FIG. 1 illustrates a system SY that includes an optical probe OP, a spectral measurement system SMS and a processing unit PU. System SY may be used in determining a tissue type TY of tissue region TR within tissue TI. Tissue region TR may be a region of the anatomy, such as the breast, the skin, the liver, the pancreas, the lung, the colon, the brain and so forth.

Optical probe OP in FIG. 1 includes distal end OPDE and three optical fibers $OF_{1..n}$. Each optical fiber has a distal end $OFDE_{1..n}$ disposed at the distal end of the optical probe OPDE, and a proximal end $OFPE_{1..n}$ that is in optical communication with spectral measurement system SMS. Spectral measurement system SMS includes at least one optical source OS and at least one optical detector OD. Each proximal end of each optical fiber $OFPE_{1..n}$ is in optical communication with one of the at least one optical source OS or one of the at least one optical detector OD, and each distal end of each optical fiber $OFDE_{1..n}$ is arranged at the distal end of the optical probe OPDE such that when the tissue region TR is in contact with the distal end of the optical probe OPDE a plurality of intersecting optical paths $IOP_{1..k}$ are defined within the tissue region TR between the at least one optical source OS and the at least one optical detector OD. Intersecting optical paths $IOP_{1..k}$ are defined for each position of optical probe OP on tissue TI; thus when optical probe OP is moved to a new position on tissue TI, a new set of intersecting optical paths are defined. Additional optical fibers may be included in a similar manner to the FIG. 1 optical probe OP.

In one exemplary system SY, Spectral measurement system SMS is configured to generate diffuse reflectance spectroscopy spectral measurement data. A broadband Tungsten halogen light source serves as optical source OS. In one configuration, two spectrometers are used to generate spectral measurement data that spans both the visible and near-infrared, NIR, spectral regions. A silicon detector is used to detect visible radiation between 400 and 1100 nm (Andor Technology, DU420ABRDD), and an InGaAs detector is used to detect NIR radiation from 800 to 1700 nm (Andor Technology, DU492A-1.7). In other configurations where e.g. only spectral measurements in the visible or NIR are desired, a single spectrometer and thus a single optical detector OD may be used. Scanning interferometer based systems may also allow for the use of a single optical detector, whereas e.g. fixed grating and optical filter-based configurations typically employ an optical detector array or multiple optical detectors. Alternative suitable optical sources for optical source OS include multiple LEDs or lasers that emit radiation within the desired spectral range, the use of solid state lasers in combination with remote phosphors, or a halogen lamp in combination with a lens system that projects the filament on optical fibers $OF_{1..n}$. The optical fibers may be spaced at a certain distance in the projected filament field. A rotating disk with multiple holes or slits may be used to ensure that only one fiber is illuminated at any point in time. By varying the speed of the disk, the illumination period can be adjusted. A halogen bulb that projects onto the end of a fiber bundle, together with a mechanical shutter between each fiber to allow for illumination of that fiber may also be used.

In general a separation between the distal ends of each radiation-emitting and radiation-receiving fiber of optical fibers $OF_{1..n}$ is preferably in the range 0.5 mm-5 mm, or the narrower range 1-4 mm, or the narrower range 1-3 mm. In one specific example a separation of 1.5 mm between the distal ends of each radiation-emitting and radiation-receiving fiber of optical fibers $OF_{1..n}$ provides each optical path with a measurement volume of approximately 1-3 $mm^3$ in tissue region TR. In the configuration illustrated in FIG. 1, three optical fibers are used; two of which serve as radiation-emitting fibers and one of which serves as a common radiation-receiving fiber. In general a preferred core diameter of each optical fiber $OF_{1..n}$ is in the range 50-600 microns, or within the narrower range 50-400 microns, or within the narrower range 100-300 microns. In one specific example each optical fiber has a core diameter of 200 microns. The common radiation-receiving optical fiber $OF_2$ receives emitted radiation that has been backscattered and/or reflected by tissue region TR. The provision of common radiation-receiving fiber $OF_2$ in FIG. 1, also provides an intersection between intersecting optical paths $IOP_1$, $IOP_2$ as illustrated by the overlapping hatching towards the distal end of optic fiber $OF_2$. In this DRS configuration the depth into tissue region TR that is probed may be increased by increasing the separation between each radiation-emitting and radiation-receiving fiber; an increase in said separation incurring a corresponding reduction in detected signal strength.

When spectral measurements in a reflectance-type configuration are desired, such as in DRS, all optical fibers $OF_{1..n}$ are preferably arranged to face a common direction as illustrated in FIG. 1. This arrangement is preferred when measuring bulky tissue, i.e. tissue TI having convenient access from only one side. Alternative spectral measurement techniques to DRS may also be used to provide the desired spectral measurement data, including fluorescence spectroscopy and Raman spectroscopy and transmission spectroscopy. Optical source(s) OS, optical detector(s) OD and corresponding optical fibers $OF_{1..n}$ may be selected and positioned at optical probe distal end OPDE in accordance with the desired spectral measurement technique. Thin tissue samples in particular may be measured in transmission configuration in which radiation-emitting and radiation-detecting optical fibers are arranged so as to face opposing directions. Corresponding optical fibers $OF_{1..n}$ may be selected according to the characteristics of the spectral measurement system, their materials and core diameter being selected in accordance with the optical wavelengths emitted by optical source OS, the surface area of tissue region TR that is to be irradiated, and the desired sensitivity of the detection by optical detector OD.

Processing unit PU may include one or more processors. Processing unit PU is in communication with spectral measurement system SMS and is configured to cause spectral measurement system SMS to generate spectral measurement data SMD corresponding to each of the plurality of intersecting optical paths $IOP_{1..k}$. Continuing the above example of DRS, spectral measurement data SMD in the form of a diffuse reflectance optical spectrum may be generated for each optical path $IOP_{1..k}$. The spectrum may for example be generated for all or a portion of the wavelength interval from approximately 400 nm to approximately 1700 nm.

Subsequently, processing unit PU generates from said spectral measurement data SMD a tissue signal $Q_{1..k}$ indicative of a tissue type TY for the respective optical path. Tissue type TY may for example be one of healthy tissue, benign tissue, malignant or tumor tissue, fat tissue, muscle tissue, or collagen tissue, elastin tissue, nerve tissue, liver tissue, colon tissue, lung tissue, or brain tissue. The invention is however not limited to these specific examples. In some implementations a tissue type is indicated in combination with a tissue optical parameter such as the content of fat, water, bile, blood, collagen, methemoglobin, beta carotene, blood oxygenation or optical scattering in the tissue region. These tissue optical parameters may also be computed as an intermediate step in determining the tissue type. In one specific example, the tissue type fat is determined. In another specific example the tissue type fat is computed as an intermediate step in determining the tissue type breast tumor tissue, which may be determined from the ratio of fat to water. In another example the content and oxygenation degree of hemoglobin is indicated in combination with the tissue type. This may be particularly useful in indicating the reliability of the so-determined tissue type since blood may obscure the optical measurements.

In one exemplary implementation, tissue signals $Q_{1..k}$ are derived from an analytical model that relates diffuse reflectance spectral measurement data to tissue type TY. The model is described below, and in more detail in the publication "A diffusion theory model of spatially resolved, steady-state diffuse reflectance for the non-invasive determination of tissue optical properties," by T. J. Farrel, M. S. Patterson and B. C. Wilson. Med. Phys. 19 (1992) p 879-888; "Farrel"; the publication "Estimation of lipid and water concentrations in scattering media with diffuse optical spectroscopy from 900 to 1600 nm", by R. Nachabé, B. H. W. Hendriks, A. E. Desjardins, M. van der Voort, M. B. van der Mark, and H. J. C. M. Sterenborg; J. Biomed. Opt. 15, 037015 (2010); "Nachabé 1"; and the publication "Estimation of biological chromophores using diffuse optical spectroscopy: benefit of extending the UV-VIS wavelength range to include 1000 to 1600 nm" by Rami Nachabé, Benno H. W. Hendriks, Marjolein van der Voort, Adrien E. Desjardins, and Henricus J. C. M. Sterenborg; Optics Express 18 (2010) p 1432; "Nachabé at al. 2".

In this widely-accepted analytical model, physiological parameters are determined by fitting the diffuse reflectance spectral measurement data from a tissue region using a custom made Matlab 7.9.0 (Mathworks, Natick, MA) algorithm.

The input arguments for the model described in Farrel are the absorption coefficient $\mu_a(\lambda)$, the reduced scattering coefficient $\mu_s'(\lambda)$ and the center-to-center distance between the emitting and collecting optical fibers at the tip of the optical probe.

The formulae used are mainly based on work of reference Nachabé 1, and reference Nachabé 2. A double power law function can be used to describe the wavelength dependence of the reduced scattering, where the wavelength $\lambda$ is expressed in nm and is normalized to a wavelength value of $\lambda_0 = 800$ nm. The parameter $\alpha$ corresponds to the reduced scattering amplitude at this specific wavelength.

$$\mu_s(\lambda) = \alpha \left( \rho_{MR} \left( \frac{\lambda}{\lambda_0} \right)^{-b} + (1 - \rho_{MR}) \left( \frac{\lambda}{\lambda_0} \right)^{-4} \right) [\text{cm}^{-1}] \quad (\text{Eq. 1})$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient $\mu_a(\lambda)$ can be computed as products of the extinction coefficients and volume fraction of the absorbers (see FIG. 2).

$$\mu_a^{Total} = f_1 \mu_a^{1} + f_2 \mu_a^{2} + f_3 \mu_a^{3} + \ldots \quad (\text{Eq. 2})$$

This total absorption $\mu_a^{Total}$ can be written as $$\mu_a^{Total} = \mu_a^{Tissue}(\lambda) + f_{other} \mu_a^{other} \quad (\text{Eq. 3})$$

where $\mu_a^{Tissue}(\lambda)$ is the absorption due to blood, water and lipid and where $\mu_a^{other}(\lambda)$ correspond to the remaining chromophores such as beta-carotene, methaemoglobin, bile, collagen, elastin.

Instead of modeling the absorption coefficient $\mu_a^{Tissue}(\lambda)$ as the sum of absorption coefficients weighted by the respective concentrations of the four chromophores of interest, it was decided to express the tissue absorption coefficient for blood, water and lipid as $$\mu_a^{Tissue}(\lambda) = C(\lambda) v_{Blood} \mu_a^{Blood}(\lambda) + v_{WL} \mu_a^{WL}(\lambda) \; [\text{cm}^{-1}] \quad (\text{Eq. 3a})$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $v_{WL} = [\text{Lipid}] + [\text{H}_2\text{O}]$, whereas $v_{Blood}$ represents the blood volume fraction for a concentration of haemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1 - \exp(-2R\mu_a^{Blood}(\lambda))}{2R\mu_a^{Blood}(\lambda)} \quad \text{(Eq. 4)}$$

where R denotes the average vessel radius expressed in cm. The absorption coefficient related to blood is given by $$\mu_a^{Blood}(\lambda) = \alpha_{BL}\mu_a^{HbO2}(\lambda) + (1-\alpha_{BL})\mu_a^{Hb}(\lambda) \; [cm^{-1}] \quad \text{(Eq. 5)}$$

where $\mu_a^{HbO2}(\lambda)$ and $\mu_a^{Hb}(\lambda)$ represent the basic extinction coefficient spectra of oxygenated haemoglobin $HbO_2$ and deoxygenated haemoglobin Hb, respectively. The oxygenated haemoglobin fraction in the total amount of haemoglobin is noted $\alpha_{BL}=[HbO_2]/([HbO_2]+[Hb])$ and is commonly known as the blood oxygen saturation. The absorption due to the presence of water and lipid in the measured tissue is defined as $$\lambda_a^{WL}(\lambda) = \alpha_{WL}\mu_a^{Lipid}(\lambda) + (1-\alpha_{WL})\mu_a^{H2O}(\lambda) \; [cm^{-1}] \quad \text{(Eq. 6)}$$

In this case the concentration of lipid related to the total concentration of lipid and water together can be written as $\alpha_{WF}=[Lipid]/([Lipid]+[H_2O])$, where [Lipid] and [$H_2O$] correspond to the concentration of lipid (density of 0.86 g/ml) and water, respectively.

This way of relating the water and lipid parameters in the expression of the absorption coefficient defined in Eq.6, rather than estimating separately the water and lipid volume fraction corresponds to a minimization of the covariance of the basic functions for fitting resulting in a more stable fit cf. the reference Nachabé 2. For further explanation and validation of this theorem reference is made to the reference Nachabé 1.

By means of the above-described algorithm, optical tissue parameters may be derived such as the scattering coefficient and absorption coefficient of different tissue chromophores: e.g. haemoglobin, oxygenated haemoglobin, water, fat etc. For further explanation see also R. Nachabé, D. J. Evers, B. H. W. Hendriks G. W. Lucassen, M. van der Voort, J. Wesseling and T. J. M. Ruers, "Effect of bile absorption coefficient on the estimation of liver tissue optical properties and related implications in discriminating healthy and tumorous samples" Biomedical Optics express 2, pp 600-614 (2011).

Figure 2:
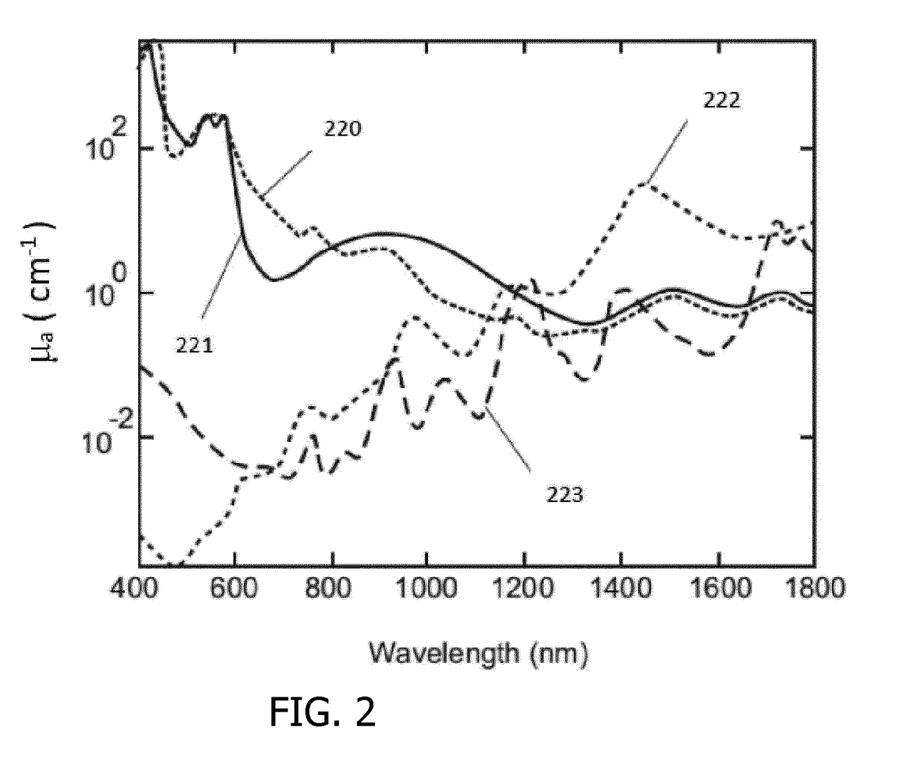
FIG. 2 illustrates optical absorption spectra in the visible and near-infrared range of some of the most important chromophores present in the human body, specifically blood, water and lipid (fat).

FIG. 2 illustrates optical absorption spectra in the visible and near-infrared range of some of the most important chromophores present in the human body, specifically blood, water and lipid (fat). The graph shows absorption coefficients of deoxygenated haemoglobin (Hb) 220, oxygenated haemoglobin ($HbO_2$) 221, water 222 and lipid 223 as a function of wavelength. Note that blood dominates the absorption in the visible range, while water and lipids dominate in the near infrared range. The graph has on its horizontal axis, the wavelength in nanometers (nm), and on its vertical axis, the absorption coefficient $\mu_a$ given in reciprocal centimeters (1/cm).

The total absorption coefficient is a linear combination of the absorption coefficients of for instance blood, water and fat (hence for each component the value of that shown in FIG. 2 multiplied by its volume fraction). By fitting the model to the measurement while using the power law for scattering, the volume fractions of the blood, water and fat as well as the scattering coefficient may be determined. When including other chromophores such as beta-carotene, bile, collagen and elastin, these can be determined in the same way.

Figure 3:
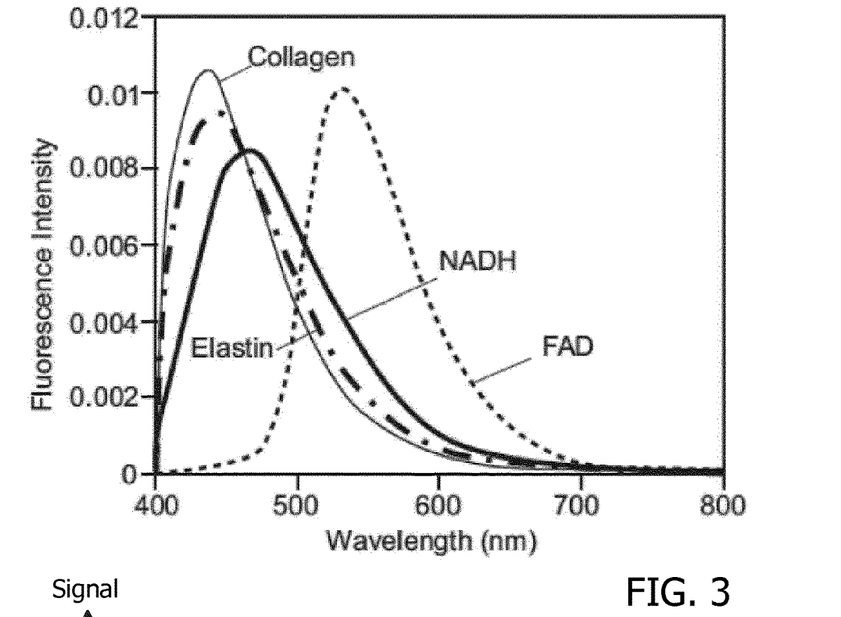
FIG. 3 illustrates a plot of the fluorescence intensity against wavelength for collagen, elastin, Nicotinamide adenine dinucleotide, i.e. NADH, and Flavin adenine dinucleotide, i.e. FAD.

In addition to diffuse reflectance measurements it is also possible to use the above described diffuse reflectance setup to measure fluorescence spectra. This permits the measurement of parameters such as collagen, elastin, NADH and FAD whose Fluorescence intensity is plotted against wavelength in FIG. 3. The ratio NADH/FAD, termed the optical redox parameter, is of interest as an indicator of the metabolic state of the tissue (see for example M. Müller and B. H. W. Hendriks, "Recovering intrinsic fluorescence by Monte Carlo modelling", J. Biomed. Optics vol. 18 (2013) p. 027009-1 to 027009-13, which can also be used to discriminate tissues.

Using the above-described techniques, a tissue signal $Q_{1..k}$ indicative of a tissue type TY for the respective optical path can be generated for the exemplary tissue types fat, collagen and elastin.

Other tissue types including for example healthy tissue, benign tissue, malignant or tumor tissue, muscle tissue, nerve tissue, liver tissue, colon tissue, lung tissue, and brain tissue can also be determined in a similar manner. For example the tissue type "breast tumor" can be determined based on a selection of the above-mentioned tissue parameters, as described in more detail in the publications De Boer 1, De Boer 2. In these publications it is reported that the fat to water ratio is a reliable indicator of the tissue type breast tumor.

Figure 4:
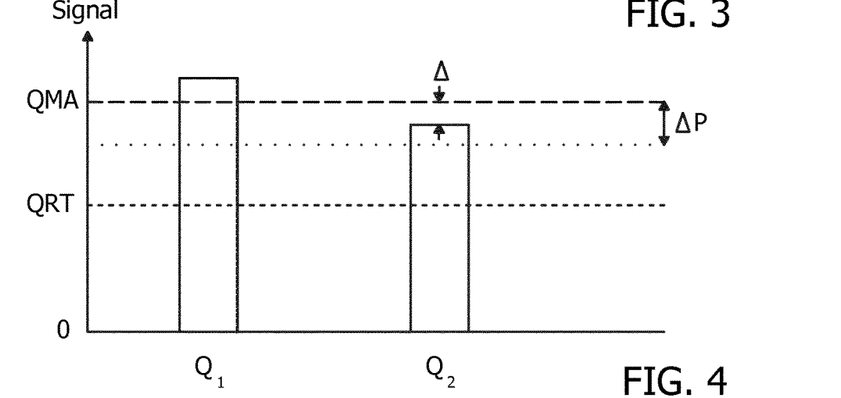
FIG. 4 illustrates exemplary tissue signals $Q_1$, $Q_2$ that are generated from spectral measurement data corresponding to each of optical paths $IOP_1$, $IOP_2$ in FIG. 1.
Figure 5:
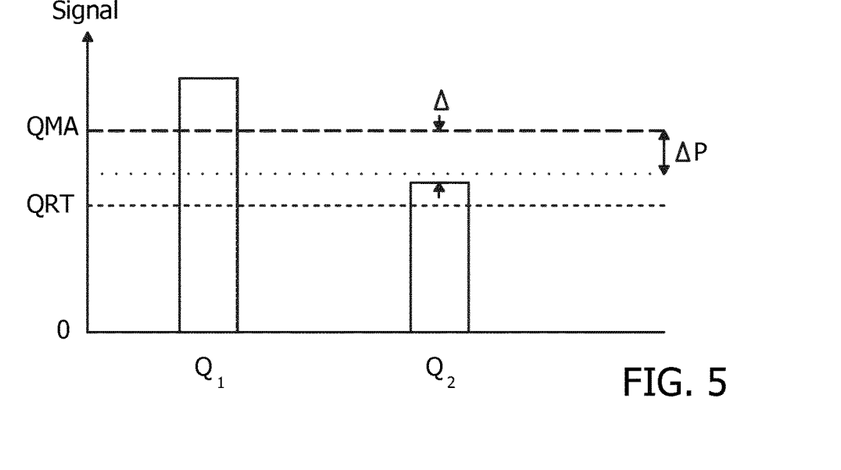
FIG. 5 illustrates another set of exemplary tissue signals $Q_1$, $Q_2$ that are generated from spectral measurement data corresponding to each of optical paths $IOP_1$, $IOP_2$ in FIG. 1.

As mentioned above, a drawback of tissue determination using existing techniques is that of false negatives. Thereto, with reference to FIG. 1, FIG. 4 and FIG. 5, processing unit PU is further configured to:

compare each tissue signal $Q_{1..k}$ with a reference threshold QRT for the tissue type TY; and to compare each tissue signal $Q_{1..k}$ with an average QMA of the tissue signals $Q_{1..k}$; and to identify at least a portion of the tissue region TR as the tissue type TY if i) every tissue signal $Q_{1..k}$ in the tissue region TR indicates that its corresponding tissue is not the tissue type TY in the comparison with the reference threshold QRT and ii) at least one of the tissue signals $Q_{1..k}$ in the tissue region TR lies between the average QMA of the tissue signals $Q_{1..k}$ and the reference threshold QRT, and a difference $\Delta$ between the at least one tissue signal $Q_{1..k}$ and the average QMA of the tissue signals $Q_{1..k}$ exceeds a predetermined value $\Delta P$.

FIG. 4 illustrates exemplary tissue signals $Q_1$, $Q_2$ that are generated from spectral measurement data corresponding to each of optical paths $IOP_1$, $IOP_2$ in FIG. 1. The magnitude of tissue signals $Q_1$, $Q_2$ is shown in arbitrary units along the vertical axis "Signal" of FIG. 4. Tissue signals $Q_1$, $Q_2$ correspond to the ratio of fat to water ratio for each of optical paths $IOP_1$, $IOP_2$ and are computed as described above from DRS measurements with particular reference to De Boer 1, De Boer 2. Tissue signals $Q_1$, $Q_2$ are thus indicative of breast tumor tissue in this example, although other tissue signals can be calculated in a similar manner. Also shown in FIG. 4 is reference threshold QRT for tissue type TY, i.e. breast tissue in this example. Reference threshold QRT may for example be an inter-patient reference threshold that discriminates between the tissue type TY, i.e. breast tumor tissue, and a different tissue type, i.e. non-tumor tissue or another tissue to breast tumor tissue, in a plurality of different patients. Reference threshold QRT may alternatively be a personal reference threshold that discriminates between the tissue type TY, i.e. breast tumor tissue, and a different tissue type, i.e. non-tumor tissue or another tissue to breast tumor tissue, and be derived from the same patient as each tissue signal $Q_{1..k}$. Tissue signals having a magnitude that is less than or equal to reference threshold QRT are indicative of breast tumor tissue, whereas tissue signals having a magnitude that exceeds reference threshold QRT indicate the absence of breast tumor tissue, or another tissue to breast tumor tissue.

Also illustrated in FIG. 4 is QMA, the average of tissue signals $Q_1$, $Q_2$. As illustrated in FIG. 4, the average of tissue signals $Q_1$, $Q_2$, i.e. QMA, exceeds reference threshold QRT, and also every individual tissue signals $Q_1$, $Q_2$ exceeds reference threshold QRT. If reference threshold QRT were used as the sole benchmark to determine tissue type it would be unsurprising to conclude that the tissue is not the tissue type in question, i.e. that it is not breast tumor tissue. In accordance with the invention, in step ii) it is further determined whether at least one of the tissue signals $Q_{1..k}$ in tissue region TR lies between the average QMA of the tissue signals $Q_{1..k}$ and the reference threshold QRT, and a difference $\Delta$ between the at least one tissue signal $Q_{1..k}$ and the average QMA of tissue signals $Q_{1..k}$ exceeds a predetermined value $\Delta P$. In FIG. 4, $\Delta \leq \Delta P$ and thus this latter condition is not met. Accordingly, at least a portion of the tissue region TR would be identified as not the tissue type; i.e. not breast tumor based on the tissue signals in FIG. 4. A different situation is illustrated in FIG. 5, which illustrates another set of exemplary tissue signals $Q_1$, $Q_2$ that are generated from spectral measurement data corresponding to each of optical paths $IOP_1$, $IOP_2$ in FIG. 1. In FIG. 5 the average of tissue signals $Q_1$, $Q_2$, i.e. QMA, exceeds reference threshold QRT, and also every individual tissue signals $Q_1$, $Q_2$ exceeds reference threshold QRT, and therefore a straightforward conclusion would be that, as in FIG. 4, that the tissue is not the tissue type in question, i.e. that it is not breast tumor tissue. However, in FIG. 5, and in accordance with step ii) of the invention it is further determined whether at least one of tissue signals $Q_{1..k}$ in tissue region TR lies between the average QMA of the tissue signals $Q_{1..k}$ and the reference threshold QRT, and a difference $\Delta$ between the at least one tissue signal $Q_{1..k}$ and the average QMA of the tissue signals $Q_{1..k}$ exceeds a predetermined value $\Delta P$. In FIG. 4, $\Delta \geq \Delta P$ and thus this latter condition is met. Accordingly, at least a portion of the tissue region TR would be identified as the tissue type; i.e. breast tumor based on the tissue signals in FIG. 4. Thus, in accordance with this step ii), any significant deviation from the average tissue signal QMA, in the direction of the tissue type, are interpreted as the tissue type. This helps to reduce false negative determinations of the tissue type, and has particular benefits in the exemplary application of breast conservation surgery. Consequently the system offers improved guidance to surgeons by ensuring there is adequate tissue removal, i.e. it reduces the percentage of positive margins that require additional surgery at a later stage.

In one implementation, if conditions i) and ii) above are met, the at least a portion of the tissue region that is identified as the tissue type TY is the portion of the tissue region corresponding to the optical path of the at least one of the tissue signals $Q_{1..k}$. In the above example where the tissue type is breast tumor tissue, this is beneficial in identifying the exact portion of tissue region TR where additional surgery may be required to excise tumor tissue.

In another implementation, if conditions i) and ii) above are met, the at least a portion of the tissue region that is identified as the tissue type TY is the entire tissue region TR. In the above example where the tissue type is breast tumor tissue, this is beneficial in generally identifying to a surgeon that at least some of the tissue in the current probe position still needs to be excised. This feature may be useful when rapidly scanning optical probe OP in multiple positions across tissue TI.

The tissue may be identified by a range of techniques including visual, audio, tactile, vibration and so forth. Specific means of such identification are described later herein.

In one implementation the predetermined value $\Delta P$ that is used for the current position of the optical probe OP is determined from the tissue signals $Q_{1..k}$ at one or more tissue regions TR' corresponding to one or more earlier positions of optical probe OP. Thereto, processing unit PU may optionally be further configured to store each tissue signal $Q_{1..k}$ for a tissue region TR corresponding to a current position of the optical probe OP on the tissue TI, and for one or more tissue regions TR' corresponding to one or more earlier positions of the optical probe OP. The predetermined value $\Delta P$ used for the current position of the optical probe OP is determined based on the tissue signals $Q_{1..k}$ for the one or more tissue regions TR' corresponding to the one or more earlier positions of the optical probe OP.

Figure 6:
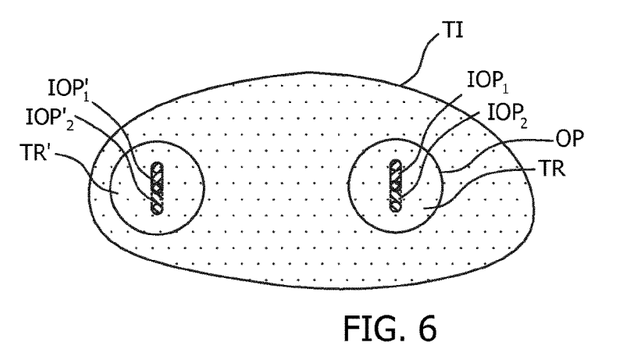
FIG. 6 illustrates a planar view of optical probe OP at a current position on tissue TI where tissue region TR is analyzed, and the same optical probe at an earlier position where tissue region TR' is analyzed.

Such a personally-determined predetermined value $\Delta P$ improves the specificity of the tissue classification by further reducing the proportion of false negative identifications of the tissue type. The predetermined value $\Delta P$ used at the current position of the optical probe OP may for example be determined based on the variation of; i.e. the spread in values of, the tissue signals $Q_{1..k}$ at the one or more tissue regions TR' at the one or more earlier positions of the optical probe OP. The variation may for example be determined based on the standard deviation or the variance of the tissue signals $Q_{1..k}$ at the one or more earlier positions of the optical probe OP. Thereto, FIG. 6 illustrates a planar view of optical probe OP at a current position on tissue TI where tissue region TR is analyzed, and the same optical probe at an earlier position where tissue region TR' is analyzed. In one scenario it is contemplated that optical probe OP is disposed initially at the positon on the left side of FIG. 6 where tissue region TR' is analyzed. Tissue region TR' is known by the surgeon to be a tumor position based on e.g. palpation or visual identification. The variation in tissue signals corresponding to optical paths $IOP'_1$, $IOP'_2$ in this known tumor tissue at tissue region TR' is used to set the predetermined value $\Delta P$ that is used for tissue identification at a subsequent, i.e. current tissue regions TR on the right side of FIG. 6. In so doing the proportion of false negative indications of the tissue type "tumor tissue" may be achieved. The personal variation of other tissue types, such as healthy tissue, may also be used in the same way to set the predetermined value $\Delta P$ for that particular type of tissue.

The above-described optical probe may be used as a stand-alone device or attached to or integrated in an interventional device. As a stand-alone device it is contemplated that the optical probe be provided in a pen-like configuration that is scanned across a tissue region during e.g. open surgery to guide a surgeon in tissue excision using a separate interventional device When combined with an interventional device, such as a tissue cutting device, a surgical knife, a biopsy device, a catheter e.g. a laser catheter, a guidewire, an electrosurgical device, an ablation device, an ultrasonic surgical device, a plasma surgery device, a cryosurgery device, a needle-based tissue removal device, a tissue suction device and so forth, it is contemplated that improved guidance maybe achieved. It is also contemplated to control the interventional device in accordance with the identified tissue type, for example by controlling the amount of power applied to the electrosurgical device.

Figure 7:
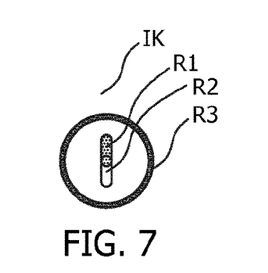
FIG. 7 illustrates an exemplary icon IK that may be displayed by display D.

The above-described system may be further provided with optional display D, as illustrated in FIG. 1. In one configuration display D is configured to display an icon IK indicative of the distal end of the optical probe, and an indication of each of the plurality of intersecting optical paths $IOP_{1..k}$. Moreover, display D may be configured to indicate, for each intersecting optical path $IOP_{1..k}$, whether the tissue signals $Q_{1..k}$ correspond to the tissue type TY. Thereto, FIG. 7 illustrates an exemplary icon IK that may be displayed by display D. Display D may for example be located on a console, or attached to the optical probe or an interventional device, or a standalone unit. Icon IK includes regions R1, R2, that correspond to each of intersecting optical paths $IOP_{1,2}$, and regions R1, R2 are used to indicate the identified tissue type. The tissue type may be identified via for example a color, a brightness, a hue or a saturation of the color, via flashing, and so forth. For example, tumor tissue type TY may be indicated by means of a red color, and healthy tissue by means of a green color. Optional region R3 in exemplary icon IK may be used to indicate that at least one of the intersecting optical paths has identified a particular tissue type, for example tumor tissue, and thereby provide a general warning to a surgeon that additional tissue should be removed from the current positon of the optical probe. This feature may be particularly beneficial when a large number of intersecting optical paths $IOP_{1..k}$ are used. In alternative implementations the identification of the tissue type TY may be via, for example tactile feedback in the form of a vibration of the optical probe, audio feedback wherein a particular frequency or sound is associated with a particular tissue type TY.

Figure 8:
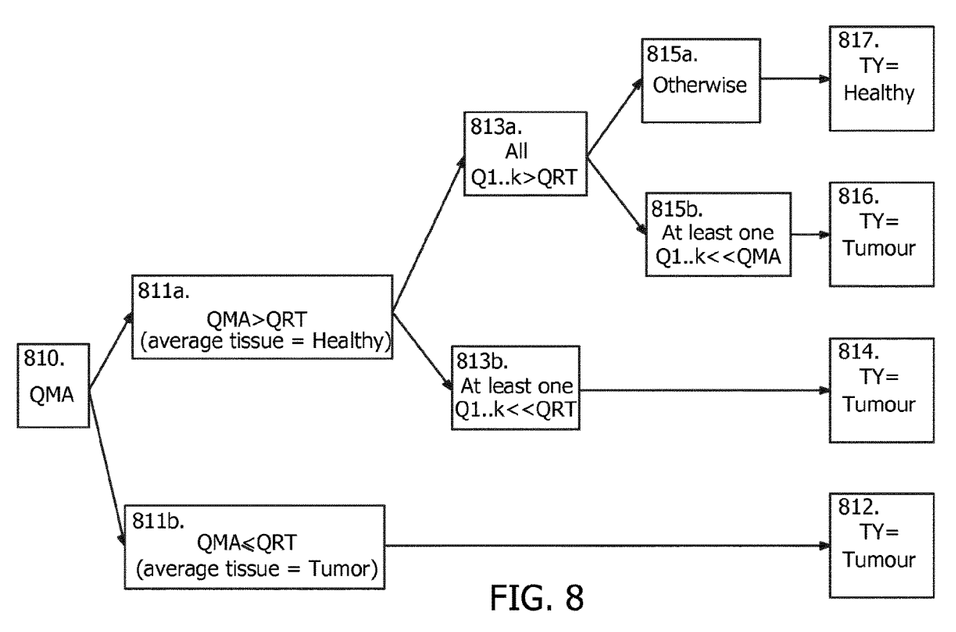
FIG. 8 illustrates a decision tree that may be used by processing unit PU in identification of a tissue type TY for the exemplary tissue type "tumor".

FIG. 8 illustrates a decision tree that may be used by processing unit PU in identification of a tissue type TY for the exemplary tissue type "tumor". With reference to FIG. 8, tissue type "tumor" is indicated by a tissue signal $Q_{1..k}$ being less than one or more threshold levels. In step 810 the average of tissue signal $Q_{1..k}$ is determined as parameter QMA. In step 811 parameter QMA is compared with a reference threshold for tumor tissue, QRT. QRT may be e.g. an inter-patient reference threshold. If QMA>QRT then in step 811a an interim conclusion is made that on average the tissue is healthy tissue. If however QMA≤QRT then a final conclusion that the tissue type TY is tumor tissue, is made in steps 811b, 812. Subsequent to step 811a, in steps 813a, b the difference between each individual tissue signal $Q_{1..k}$ and reference threshold QRT is determined. If at least one of tissue signals $Q_{1..k}$ is substantially less than reference threshold QRT then a final conclusion that the tissue type TY is tumor tissue, is made in steps 813b, 814. If, alternatively, all tissue signals $Q_{1..k}$ exceed reference threshold QRT then in step 813a is followed. If, subsequent to step 813a, at least one of tissue signals $Q_{1..k}$ is substantially less than the average of tissue signals $Q_{1..k}$, i.e. QMA, then a final conclusion that the tissue type is tumor, is made in steps 815b, 816. In the alternative, then following step 813a, steps 815a, 817 result in a final conclusion that the tissue type is not tumor tissue, i.e. it is healthy or benign tissue. Steps 813a, 815b, 816 reduce the number of false negative indications, i.e. they reduce the number of incorrect indications that tissue is healthy because significant individual measurement deviations from their average are considered to be indicative of tumor tissue. This is in spite of all individual tissue signals being indicative of healthy tissue in the comparison with the reference threshold QRT.

By substantially less than a value, it is meant that the deviation is greater than a predetermined amount from that value, which deviation may be for example related to the variation or the variance or the standard deviation of that value. Similar decision trees can of course be made when a tissue type TY is indicated by the presence of tissue signals that exceeds one or more threshold levels.

Alternative optical probe designs to the one illustrated in FIG. 1 are shown in FIG. 9-FIG. 12.

Figure 9:
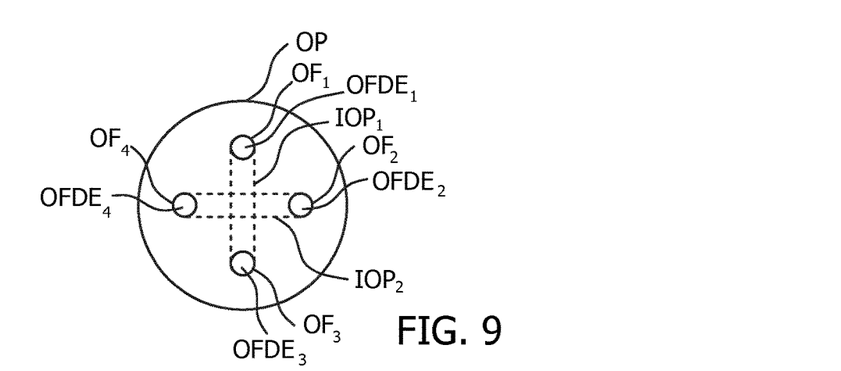
FIG. 9 illustrates a second embodiment of an optical probe OP in which two separate intersecting optical paths $IOP_1$, $IOP_2$ are provided between the distal ends $OFDE_{1..4}$ of four optical fibers.

FIG. 9 illustrates a second embodiment of an optical probe OP in which two separate intersecting optical paths $IOP_1$, $IOP_2$ are provided between the distal ends $OFDE_{1..4}$ of four optical fibers. In this example, corresponding optical fibers $OF_1$, $OF_2$ are in communication with one or more optical sources, and optical fibers $OF_3$, $OF_4$ are in communication with one or more optical detectors in spectral measurement system SMS. Intersecting optical paths $IOP_1$, $IOP_2$ intersect at a point elevated from the plane of the figure in a similar manner to that illustrated in the cross sectional view in FIG. 1. Tissue signals $Q_{1..k}$ for a given position of optical probe OP may be measured simultaneously or consecutively.

Figure 10:
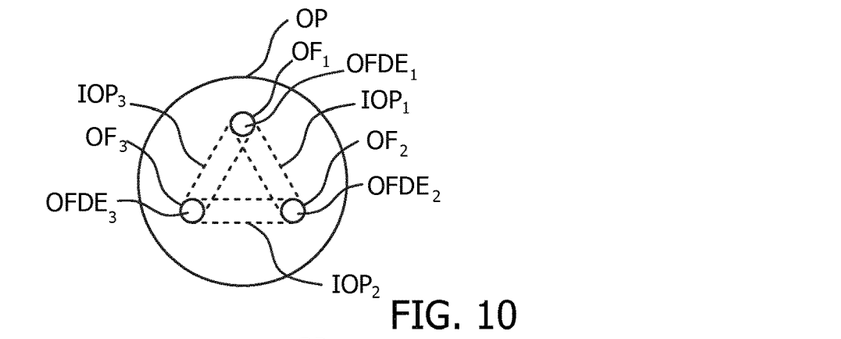
FIG. 10 illustrates a third embodiment of an optical probe OP in which three separate intersecting optical paths $IOP_1$, $IOP_2$, $IOP_3$ are provided between the distal ends $OFDE_{1..3}$ of three optical fibers.

In some embodiments the optical paths are hard-wired, whereas in other embodiments these are changed by means of optical switches that change the function of an optical fiber between a radiation-emitting and a radiation-receiving optical fiber. Thereto, FIG. 10 illustrates a third embodiment of an optical probe OP in which three separate intersecting optical paths $IOP_1$, $IOP_2$, $IOP_3$ are provided between the distal ends $OFDE_{1..3}$ of three optical fibers. In FIG. 10 for example, intersecting optical paths $IOP_{1..3}$ may be optically hard-wired such that corresponding optical fibers $OF_1$, $OF_3$ act as radiation-emitting fibers and $OF_2$ acts as a radiation-receiving fiber and such that the optical paths intersect at $OFDE_2$; or one or more optical switches in spectral measurement system SMS may be used to for example cause optical fibers $OF_1$ and $OF_2$ to at one instant act as radiation-emitting and radiation-receiving fibers respectively, and at a later instant cause optical fibers $OF_2$ and $OF_3$ to act as radiation-emitting and radiation-receiving fibers respectively, and at a later instant still cause optical fibers $OF_3$ and $OF_4$ to act as radiation-emitting and radiation-receiving fibers respectively. In this latter example the tissue signals may therefore be measured consecutively with optical probe OP in a fixed position respective tissue TI, and the intersection in the optical paths may also be moved spatially with optical probe OP in a fixed position respective tissue TI. Moreover, the lengths of each optical path may be the same for all intersecting optical paths, as illustrated in FIG. 9 and FIG. 10, or this may be varied by using different separations between the distal ends of radiation-receiving and radiation-emitting optical fibers that define each optical path. This may be useful in probing different depths of tissue TI.

Figure 11:
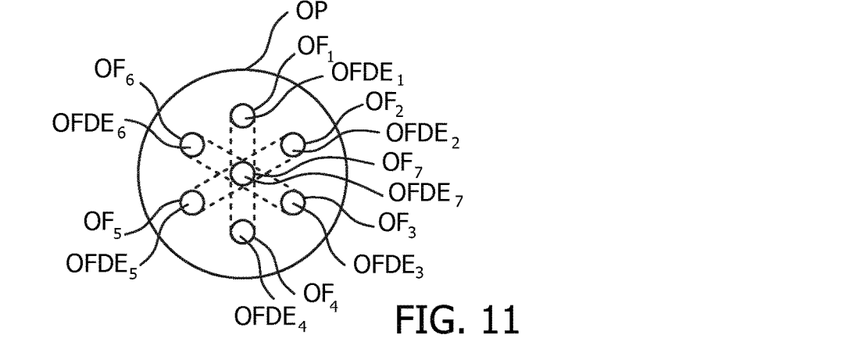
FIG. 11 illustrates a fourth embodiment of an optical probe OP in which six intersecting optical paths are provided between the distal ends of each of six radiation-emitting fibers $OFDE_{1..6}$ and one radiation-receiving optical fiber $OF_7$.

FIG. 11 illustrates a fourth embodiment of an optical probe OP in which six intersecting optical paths are provided between the distal ends of each of six radiation-emitting fibers $OFDE_{1..6}$ and one radiation-receiving optical fiber OF A. The six optical paths intersect at optical fiber distal end $OFDE_7$. In the configuration of FIG. 11, optical signals may be measured consecutively via radiation-receiving optical fiber $OF_7$, which simplifies the optical detector design in that a single optical detector or spectrometer may be used.

Figure 12:
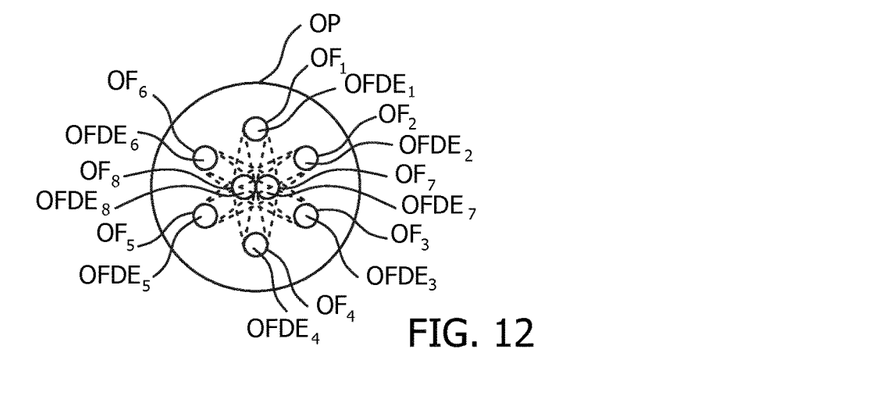
FIG. 12 illustrates a fifth embodiment of an optical probe OP in which twelve intersecting optical paths are provided between the distal ends of each of six radiation-emitting fibers $OFDE_{1..6}$ and each of two radiation-receiving optical fibers $OF_7$, $OF_8$.

FIG. 12 illustrates a fifth embodiment of an optical probe OP in which twelve intersecting optical paths are provided between the distal ends of each of six radiation-emitting fibers $OFDE_{1..6}$ and each of two radiation-receiving optical fibers $OF_7$, $OF_8$. The twelve optical paths intersect in the vicinity of optical fiber distal ends $OFDE_7$, $OFDE_8$. In one implementation, corresponding optical fibers $OF_{7, 8}$ may be in optical communication with the same spectrometer and thus serve to improve the sensitivity of the optical probe. In another implementation optical fibers $OF_{7, 8}$ may each connect to a separate spectrometer that is configured to measure a different spectral range. For example, $OF_7$ may be in optical communication with a visible spectrometer and $OF_8$ may be in optical communication with a visible spectrometer. Additional radiation-receiving optical fibers to $OF_{7, 8}$ may also be used in the form of a fiber bundle to further increase sensitivity of spectral measurement system SMS.

Thus, FIG. 9-FIG. 12 illustrate exemplary configurations of optical probe OP, and it is to be appreciated that additional optical fibers and optical paths may be included in a similar manner.

In one embodiment a computer program product comprises instructions which when executed on a processor of the processing unit of the system described in FIG. 1, cause the processor to carry out the method steps of:

causing spectral measurement system SMS to generate spectral measurement data SMD corresponding to each of the plurality of intersecting optical paths $IOP_{1..k}$, and to generate from said spectral measurement data SMD a tissue signal $Q_{1..k}$ indicative of a tissue type TY for the respective optical path;

comparing each tissue signal $Q_{1..k}$ with a reference threshold QRT for the tissue type TY; and comparing each tissue signal $Q_{1..k}$ with an average QMA of the tissue signals $Q_{1..k}$; and identifying at least a portion of the tissue region TR as the tissue type TY if i) every tissue signal $Q_{1..k}$ in the tissue region TR indicates that its corresponding tissue is not the tissue type TY in the comparison with the reference threshold QRT and ii) at least one of the tissue signals $Q_{1..k}$ in the tissue region TR lies between the average QMA of the tissue signals $Q_{1..k}$ and the reference threshold QRT, and a difference $\Delta$ between the at least one tissue signal $Q_{1..k}$ and the average QMA of the tissue signals $Q_{1..k}$ exceeds a predetermined value $\Delta P$.

Any of the method steps disclosed herein, particularly those described in relation to FIG. 8 may also be optionally carried out by processing unit PU. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium.

Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary, a system SY for determining a tissue type TY of a tissue region TR has been provided in which the distal ends $OFDE_{1..n}$ of at least three optical fibers define a plurality of intersecting optical paths $IOP_{1..k}$ within the tissue region TR. A tissue signal $Q_{1..k}$ indicative of a tissue type TY for the respective optical path $IOP_{1..k}$ is generated from said spectral measurement data SMD corresponding to each of the plurality of intersecting optical paths $IOP_{1..k}$. Each tissue signal $Q_{1..k}$ is compared with a reference threshold QRT for the tissue type, and with an average of the tissue signals QMA. At least a portion of the tissue region is identified as the tissue type TY if i) every tissue signal $Q_{1..k}$ in the tissue region TR indicates that its corresponding tissue is not the tissue type TY in the comparison with the reference threshold QRT and ii) at least one of the tissue signals $Q_{1..k}$ in the tissue region TR lies between the average QMA of the tissue signals $Q_{1..k}$ and the reference threshold QRT, and a difference $\Delta$ between the at least one tissue signal $Q_{1..k}$ and the average QMA of the tissue signals $Q_{1..k}$ exceeds a predetermined value $\Delta P$.

Various embodiments and options have been described in relation to the tissue type determination system, and it is noted that the various embodiments may be combined to achieve further advantageous effects.

The invention claimed is:

1. A system for determining a tissue type of a tissue region of a tissue, the system comprising:
   an optical probe comprising a distal end and at least three optical fibers, each optical fiber having a distal end disposed at the distal end of the optical probe and a proximal end that is in optical communication with a spectral measurement system,
   wherein the spectral measurement system comprises at least one optical source and at least one optical detector,
   wherein each proximal end of each optical fiber is in optical communication with one of the at least one optical source or one of the at least one optical detector, and
   wherein each distal end of each optical fiber is arranged at the distal end of the optical probe such that when the tissue region is in contact with the distal end of the optical probe, a plurality of intersecting optical paths are defined within the tissue region between the at least one optical source and the at least one optical detector; and
   a processor in communication with the spectral measurement system, the processor configured to:
   cause the spectral measurement system to generate spectral measurement data corresponding to each of the plurality of intersecting optical paths,
   generate from the spectral measurement data a tissue signal indicative of a tissue type for the respective optical path,
   compare each tissue signal with a reference threshold for the tissue type,
   compare each tissue signal with an average of tissue signals of the plurality of intersecting optical paths, and
   identify at least a portion of the tissue region as the tissue type if i) every tissue signal in the tissue region indicates that its corresponding tissue is not the tissue type in the comparison with the reference threshold and ii) at least one of the tissue signals in the tissue region lies between the average of the tissue signals and the reference threshold, and a difference between the at least one tissue signal and the average of the tissue signals exceeds a predetermined value.

2. The system according to claim 1, wherein the reference threshold is an inter-patient reference threshold that discriminates between the tissue type and a different tissue type in a plurality of different patients.

3. The system according to claim 1, wherein the reference threshold is a personal reference threshold that discriminates between the tissue type and a different tissue type and is derived from the same patient as each tissue signal.

4. The system according to claim 1, wherein the at least a portion of the tissue region that is identified as the tissue type is the portion of the tissue region corresponding to the optical path of the at least one of the tissue signals.

5. The system according to claim 1, wherein the at least a portion of the tissue region that is identified as the tissue type is the entire tissue region.

6. The system according to claim 1, wherein the processor is further configured to:
store each tissue signal for a tissue region corresponding to a current position of the optical probe on the tissue, and for one or more tissue regions corresponding to one or more earlier positions of the optical probe on the tissue, and
determine the predetermined value used for the current position of the optical probe based on the tissue signals for the one or more tissue regions (TR') corresponding to the one or more earlier positions of the optical probe (OP).

7. The system according to claim 6, wherein the processor is configured to determine the predetermined value used for the current position of the optical probe based on a variation of the tissue signals at the one or more tissue regions corresponding to the one or more earlier positions of the optical probe.

8. The system according to claim 1, wherein the tissue signal is indicative of one of healthy tissue, benign tissue, malignant or tumor tissue, fat tissue, muscle tissue, collagen tissue, elastin tissue, nerve tissue, liver tissue, colon tissue, lung tissue, or brain tissue.

9. The system according to claim 1, wherein the processor is further configured to provide an indication of an optical parameter of the tissue region, wherein the optical parameter is at least one of: fat content, water content, beta carotene content, bile content, blood content, blood oxygenation, collagen content, methemoglobin content, and optical scattering.

10. The system according to claim 1, further comprising an interventional device with the optical probe attached to or is integrated in the interventional device.

11. The system according to claim 10, wherein the interventional device is one of: tissue cutting device, a surgical knife, a biopsy device, a catheter, a guidewire, an electrosurgical device, an ultrasonic surgical device, a plasma surgery device, a cryosurgery device, a needle-based tissue removal device, a tissue suction device, or an ablation device.

12. The system according to claim 1, further comprising a display configured to:
display an icon indicative of the distal end of the optical probe, and an indication of each of the plurality of intersecting optical paths; and
indicate, for each intersecting optical path whether the tissue signals corresponds to the tissue type.

13. A non-transitory computer-readable storage medium having stored a computer program comprising instructions which when executed by a processor, cause the processor to:
cause a spectral measurement system to generate spectral measurement data corresponding to each of a plurality of intersecting optical paths and to generate from the spectral measurement data a tissue signal indicative of a tissue type for the respective optical path,
wherein the spectral measurement system comprises at least one optical source and at least one optical detector, each proximal end of each optical fiber of an optical probe is in optical communication with one of the at least one optical source or one of the at least one optical detector, each distal end of each optical fiber arranged at the distal end of the optical probe such that when the tissue region is in contact with the distal end of the optical probe, a plurality of intersecting optical paths are defined within the tissue region between the at least one optical source and the at least one optical detector;
compare each tissue signal with a reference threshold for the tissue type;
compare each tissue signal with an average of tissue signals of the plurality of intersecting optical paths; and
identify at least a portion of a tissue region as the tissue type if i) every tissue signal in the tissue region indicates that its corresponding tissue is not the tissue type in the comparison with the reference threshold and ii) at least one of the tissue signals in the tissue region lies between the average of the tissue signals and the reference threshold and a difference between the at least one tissue signal and the average of the tissue signals exceeds a predetermined value.

14. The non-transitory computer-readable storage medium according to claim 13, wherein the reference threshold is an inter-patient reference threshold that discriminates between the tissue type and a different tissue type in a plurality of different patients.

15. The non-transitory computer-readable storage medium according to claim 13, wherein the reference threshold is a personal reference threshold that discriminates between the tissue type and a different tissue type and is derived from the same patient as each tissue signal.

16. The non-transitory computer-readable storage medium according to claim 13, wherein the at least a portion of the tissue region that is identified as the tissue type is the portion of the tissue region corresponding to the optical path of the at least one of the tissue signals.

17. A computer-implemented method for determining a tissue type of a tissue region, the method comprising:
causing a spectral measurement system to generate spectral measurement data corresponding to each of a plurality of intersecting optical paths and generate from the spectral measurement data a tissue signal indicative of a tissue type for the respective optical path,
wherein the spectral measurement system comprises at least one optical source and at least one optical detector, each proximal end of each optical fiber of an optical probe is in optical communication with one of the at least one optical source or one of the at least one optical detector, each distal end of each optical fiber arranged at the distal end of the optical probe such that when the tissue region is in contact with the distal end of the optical probe, a plurality of intersecting optical paths are defined within the tissue region between the at least one optical source and the at least one optical detector;

comparing each tissue signal with a reference threshold for the tissue type;
comparing each tissue signal with an average of tissue signals of the plurality of intersecting optical paths; and
identify at least a portion of a tissue region as the tissue type if i) every tissue signal in the tissue region indicates that corresponding tissue is not the tissue type in the comparison with the reference threshold and ii) at least one of the tissue signals in the tissue region lies between the average of the tissue signals and the reference threshold, and a difference between the at least one tissue signal and the average of the tissue signals exceeds a predetermined value.

18. The method according to claim 17, wherein the reference threshold is an inter-patient reference threshold that discriminates between the tissue type and a different tissue type in a plurality of different patients.

19. The method according to claim 17, wherein the reference threshold is a personal reference threshold that discriminates between the tissue type and a different tissue type and is derived from the same patient as each tissue signal.

20. The method according to claim 17, wherein the at least a portion of the tissue region that is identified as the tissue type is the portion of the tissue region corresponding to the optical path of the at least one of the tissue signals.

* * * * *